United States Patent [19]

Schrauzer

[11] Patent Number: 5,236,697
[45] Date of Patent: Aug. 17, 1993

[54] PRODUCT FOR TREATMENT OF ACNE AND OTHER SKIN CONDITIONS

[76] Inventor: Gerhard N. Schrauzer, 175 Alameda Blvd., Coronado, Calif. 92118

[21] Appl. No.: 849,996

[22] Filed: Mar. 10, 1992

Related U.S. Application Data

[63] Continuation of Ser. No. 599,365, Oct. 18, 1990, abandoned.

[51] Int. Cl.⁵ .............................................. A61L 9/04
[52] U.S. Cl. ...................................... 424/45; 424/70; 562/122; 252/182.18; 252/392
[58] Field of Search ............... 424/70, 45; 562/122; 71/94; 252/182.18, 392

[56] References Cited

U.S. PATENT DOCUMENTS

| | | | |
|---|---|---|---|
| 3,860,528 | 1/1975 | Dewitt | 252/182.18 |
| 3,943,174 | 3/1976 | Ellis | 562/122 |
| 4,302,354 | 11/1981 | Giede | 422/12 |
| 4,849,211 | 7/1989 | Schrauzer | 424/70 |
| 4,886,545 | 12/1989 | Peck | 71/94 |

Primary Examiner—Thurman K. Page
Assistant Examiner—William E. Benston
Attorney, Agent, or Firm—Christie, Parker & Hale

[57] ABSTRACT

The straight-chain terminal olefinic hydrocarbon n-decene-1 and compositions containing n-decene-1 are effective in the treatment of minor localized skin infections, inflammatory skin conditions and soreness when applied topically to the skin. Typically, the product comprises from about 5 to 100 volume percent of pure n-decene-1. However, mixtures of n-decene-1 with inert solvents or fillers for use in lotions, creams, gels and sprays can also be used.

9 Claims, No Drawings

PRODUCT FOR TREATMENT OF ACNE AND OTHER SKIN CONDITIONS

This is a continuation of application Ser. No. 599,365, filed Oct. 18, 1990, now abandoned.

BACKGROUND OF THE INVENTION

This invention relates in general to skin care products, more specifically to product formulations for treating minor localized skin infections, inflammatory conditions and soreness.

Among the cosmetic and skin treatment products which are presently available, many contain paraffinic hydrocarbons such as present in vaseline, mineral oil, petrolatum or fatty substances of plant or animal origin such as lanolin, animal fats or synthetic fatty substances of high molecular weight. These substances, once applied, remain on the skin. They clog the skin and by preventing skin respiration may be comedogenic, cause bacterial infections, skin irritations and allergic reactions. The undesirable properties may be avoided by using selected fractions of saturated hydrocarbons of shorter chain lengths than predominantly present in vaseline, mineral oil or petrolatum, namely n-decane, n-undecane, n-dodecane, representing the saturated hydrocarbons with chain lengths of 10, 11 and 12 carbon atoms. These hydrocarbons do not accumulate on the skin as they slowly evaporate due to their comparatively high vapor pressures at ambient temperature. Their use in formulations for the treatment of acne and related skin disorders was claimed in U.S. Pat. No. 4,849,211.

SUMMARY OF THE INVENTION

All hydrocarbons claimed in U.S. Pat. No. 4,849,211 as vehicles belong to the class of saturated, or paraffinic hydrocarbons in conjuncture with squalene, a constituent of the skin, as the active ingredient. The present invention now is claiming the use of one specific member of the group of unsaturated, or olefinic, hydrocarbons for the topical treatment of acne and other skin disorders. While paraffinic hydrocarbons contain only single carbon-carbon bonds and units such as —CH$_2$—CH$_2$—, olefinic hydrocarbons may contain one or more double bonds indicated by units such as CH$_2$=CH— and —CH=CH—. Compounds with one olefinic double bond are called monoolefins. If the double bond is positioned at the end of the carbon chain, such olefins are called "terminal monoolefins". The carbon chain may be straight or branched. Straight-chain olefins are called "normal olefins"; in the common nomenclature, this structural feature is indicated by the prefix "n-". Thus, n-decene-1, which is also sometimes written as 1-n-decene or simply 1-decene, is the straight-chain terminal monoolefin with 10 carbon atoms which has the formula

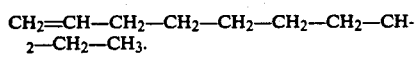

Terminal monoolefins of chain lengths of at least 9 carbon atoms and not exceeding 11 carbon atoms are active in products for the treatment and control of acne, folliculitis and other localized skin disorders.

Terminal olefins are present in crude petroleum distillates. They are, however, also found in living systems and natural products. For example, decene-1 is found in Conifer leaf oils, see Chemical Abstracts 90, 147976q, or Rue root oil, Chemical Abstracts 90, 127380n.

Nonene-1 is present in defensive secretions of rove beetle, Chemical Abstracts 98, 50753s. Nonene-1 was also detected in certain mushrooms, Chemical Abstracts 99, 69120a, while octene-1 was shown to be present in frozen berry volatiles, Chemical Abstracts 104, 18790h.

The boiling points of several terminal n-olefins as taken from Beilstein's Handbook of Organic Chemistry, are as follows: n-heptene-1, 98°–99°; n-octene-1, 122°–122.1°, n-nonene-1, 146°, n-decene-1, 170°–172°, n-undecene-1, 192.6°; n-dodecene, 213°.

It now has been found that terminal monoolefins of appropriate chain length have surprisingly strong antibacterial, antiinflammatory and other beneficial effects on the human skin. This property is not shared by the corresponding saturated hydrocarbon, n-decane, and thus must be attributed to an essential extent to the presence of the olefinic double bond in the molecule. The olefinic double bond, is contrast to the carbon-carbon single bond, is chemically reactive. Of particular importance within the context of the present invention are the reactions of olefinic double bonds with oxygen and oxygen radicals as these reactions take place at ambient temperatures, giving rise to the formation of peroxides and hydroperoxides. Peroxides contain oxygen-oxygen, —O—O—, bonds as indicated by the formula:

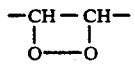

Hydroperoxides contain the unit —O—O—H as shown by the formula:

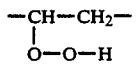

As olefins are scavengers of oxygen and oxygen radicals, they belong to the group of antioxidants. However, the organic peroxides and hydroperoxides which are formed in the reactions of olefins with oxygen are chemically reactive species; moreover, they are known to exhibit antibacterial properties. Thus, many commercial antiacne products presently in use containing organic peroxides, notably benzoyl peroxide, as the active ingredient. One example "Clearasil", distributed by Vicks Toiletry Products, is listed in "Physicians Desk Reference" (PDR, Charles Baker Publisher, 1982), to contain 5% benzoyl peroxide.

The ability of olefins to react with oxygen or oxygen radicals at ambient temperature is important for the treatment of acne and related skin conditions, notably bacterial infections and inflammatory reactions as oxygen radicals are formed as part of the pathological processes. Oxygen radicals are known to damage cell membranes and cell constituents. The body normally utilizes enzymes such as catalase, glutathione peroxidase and the antioxidants vitamin A and E to protect itself against the injurious effects of oxygen radicals. In infected skin, excessive amounts of oxygen radicals are produced. This gives rise initially to inflammatory responses visible by reddening of the skin; if sufficiently severe, lesions may appear which open the way to secondary infection by bacteria such as stapylococcus aureus, Salmonella sp., and others.

The chief embodiment of the present invention is that certain terminal olefins have a pronounced effect against some form of acne and folliculitis, both of which represent skin affectation caused by infectious bacterial agents. Moreover, said olefins also inhibit localized inflammatory skin conditions. Not all olefins are equally effective, however. A key factor which determines the efficacy and practical usefulness is their chain-length and the position and number of double bonds in the molecule. Because of these requirements, the number of compounds is severely limited. I now have found on the basis of practical experiments that n-decene-1 is one such compound.

For example, excellent results in the treatment of minor skin infections have been achieved by applying a small amount of pure n-decene-1 directly on the affected areas. Often the benefical effects are noticeable within minutes after the application: Inflamed areas attain their normal color, puss-filled pustules dry up, and the healing of open skin lesions is initiated. The reasons for the special properties of n-decene-1 may be summarized as follows: Because of its low molecular weight, n-decene-1 has a penetrating action onto the human skin. Because of its boiling point of 170°–172°, its vapor pressure at ambient temperature is sufficiently high to cause its complete evaporation within 5–10 minutes, which is optimal for the abovementioned applications. Thus, n-decene-1 can be applied repeatedly without causing an undesirable accumulation on the skin. This is no longer the case with n-undecene-1 and n-dodecene-1; both of these higher-boiling olefinic hydrocarbons already display a clogging effect if brought onto the skin due to their lower volatility. However, it is also important with respect to the present invention, that none of the lower n-terminal monoolefins can be used with advantage over n-decene-1. Because of their lower boiling points their vapor pressures at ambient temperature are too high and the residence times on the skin are too short. They also have pungent, unpleasant odors, and due to their low flame-points pose a serious fire hazard. We have also found that internal olefins such as decene-5, $CH_3(CH_2)_3CH=CH(CH_2)_3CH_3$, for example, in general were found less effective than n-decene-1. Similarly, cycloolefins such as cyclooctene, cylododecene and cyclododecatriene could not be considered for skin-care applications due to their irritating effects onto the human skin, their unpleasant or strong odors, or other undesirable properties. Straight-chain olefins with two, three or more double bonds are known as diolefins, triolefins or polyolefins. These are more reactive than the monoolefins and may undergo polymerization reactions. They also react with oxygen, but compared to the monoolefins, these reactions occur too rapidly for their intended use, and the products of autoxidation are often severely irritating or otherwise toxic to normal skin. Thus it was confirmed that decene-1 possesses a rare combination of properties which render it practically useful and therefore this compound alone is the essential embodiment of the present invention.

Decene-1 is preferably applied as such but may also be applied as a spray, or dissolved in inert solvents. It may also be added. As solvents, paraffinic hydrocarbons such as n-decane, n-undecane, n-dodecane may be employed at various proportions. Alcoholic solvents such as isopropanol or ethyl alcohol, may also be used. The product may be added to gels, soaps or creams; for use in sprays, it may be mixed with an inert propellant. It may also be added in amounts of up to 20% to an inert filler. Finally, n-decene-1 may also be used as a solvent for lipid-soluble drugs, hormones, vitamins and other substances that are applied on the skin. Details of the invention, and of certain preferred embodiments thereof will be further exemplified upon reference to the following examples. Parts are by weight and percentage by volume unless otherwise indicated.

EXAMPLE I

A female subject aged 21 years with acneform skin eruptins applied several drops of n-decene-1 directly onto the affected areas. A striking improvement of the treated areas became visually apparent within a few hours following the application, with most of them clearing after 48 hours.

EXAMPLE II

A male subject of 57 years with localized folliculitis consisting of subcorneal pustules at the opening of hair follicles with inflammation in the upper dermis, applied n-undecene-1 topically 3 times onto the affected areas over a period of 30 minutes. The swelling and the inflammation of the affected areas disappeared rapidly.

EXAMPLE III

A male subject with localized folliculitis observed complete relief upon the topical application of a solution of 10% decene-1 in ethyl alcohol.

EXAMPLE IV

A male subject experienced swelling and pain typical during the beginning formation of a carbuncle. Application of n-decene-1 brought almost instantaneous relief of pain, rapid disappearance of the erythema and swelling.

Other variations, applications and ramifications of this invention will occur to those skilled in the art upon reading this disclosure. Those intended to be included within the scope of this invention are defined in the appended claims.

What is claimed is:

1. A method for treating localized skin disorders comprising:
    applying topically to the skin disorder a composition consisting essentially of a terminal monoolefin having a chain length in the range of from 9 to 11 carbon atoms.
2. A method as recited in claim 1 wherin the terminal monoolefin is n-decene-1.
3. A method as recited in claim 2 comprising applying the monoolefin in a composition including a pharmaceutically acceptable carrier for application of the composition as a spray, cream or gel.
4. A method as recited in claim 3 comprising applying the monoolefin in a composition including adjuvants selected from the group consisting of lipid-soluble drugs, fatty acids, hormones, and vitamins.
5. A method as recited in claim 1 comprising applying the monoolefin in a composition including a pharmaceutically acceptable carrier for application of the composition as a spray, cream or gel.
6. A method as recited in claim 5 comprising applying the monoolefin in a composition including adjuvants selected from the group consisting of lipid-soluble drugs, fatty acids, hormones, and vitamins.

7. A method as recited in claim 1 comprising applying the monoolefin in a composition including adjuvants selected from the group consisting of lipid-soluble drugs, fatty acids, hormones, and vitamins.

8. A skin care product for treatment and control of localized skin disorders consisting essentially of a terminal monoolefin having a chain length in the range of from 9 to 11 carbon atoms and a pharmaceutically acceptable material selected from the group consisting of carriers for application of the composition as a spray, cream or gel, lipid-soluble drugs, fatty acids, hormones, and vitamins and.

9. A product as recited in claim 8 wherein the terminal monoolefin is n-decene-1.

* * * * *

UNITED STATES PATENT AND TRADEMARK OFFICE
CERTIFICATE OF CORRECTION

PATENT NO. : 5,236,697
DATED      : August 17, 1993
INVENTOR(S): Gerhard N. Schrauzer It is certified that error appears in the above-indentified patent and that said Letters Patent is hereby corrected as shown below:

Column 4, line 14, change "eruptins" to -- eruptions --.

Signed and Sealed this

Fourteenth Day of June, 1994

Attest:

BRUCE LEHMAN

Attesting Officer    Commissioner of Patents and Trademarks